(12) United States Patent
Temsamani et al.

(10) Patent No.: US 7,365,055 B2
(45) Date of Patent: Apr. 29, 2008

(54) DERIVATIVES OF MORPHINE-6-GLUCURONIDE, PHARMACEUTICAL COMPOSITIONS CONTAINING THEM, THEIR PREPARATION METHOD AND THEIR USES

(75) Inventors: Jamal Temsamani, Nimes (FR); Roger Lahana, Nimes (FR); Patrick Mouchet, Fourques (FR)

(73) Assignee: BTG International Limited (GB)

( * ) Notice: Subject to any disclaimer, the term of this patent is extended or adjusted under 35 U.S.C. 154(b) by 118 days.

(21) Appl. No.: 10/583,992

(22) PCT Filed: Dec. 22, 2004

(86) PCT No.: PCT/FR2004/003342

§ 371 (c)(1),
(2), (4) Date: Jun. 22, 2006

(87) PCT Pub. No.: WO2005/063263

PCT Pub. Date: Jul. 14, 2005

(65) Prior Publication Data

US 2007/0116665 A1    May 24, 2007

(30) Foreign Application Priority Data

Dec. 22, 2003   (FR) .................... 03 15160

(51) Int. Cl.
*A61K 31/70*  (2006.01)
*A61K 31/7042*  (2006.01)
*A61K 31/7028*  (2006.01)

(52) U.S. Cl. .............. 514/27; 514/25; 536/4.1; 536/17.4; 536/17.5; 536/17.9; 536/18.5

(58) Field of Classification Search ............. 514/27, 514/25; 536/4.1, 17.4, 17.5, 17.9, 18.5
See application file for complete search history.

(56) References Cited

FOREIGN PATENT DOCUMENTS

| EP | 0 816 375 | 1/1998 |
|---|---|---|
| FR | 2 821 272 | 8/2002 |

*Primary Examiner*—Shaojia Anna Jiang
*Assistant Examiner*—Michael C. Henry
(74) *Attorney, Agent, or Firm*—Hunton & Williams LLP (57) ABSTRACT

The invention relates to novel derivatives of morphine-6-glucuronide, the preparation method thereof and the uses of same in therapy, for example, as analgesics.

23 Claims, 6 Drawing Sheets

M6G-Cys-OMe

M6G-Cys-OEt

M6G-Cys-OH

M6G-Cys-DEA

M6G-Cya-Cya-PEG20000

DERIVATIVES OF MORPHINE-6-GLUCURONIDE, PHARMACEUTICAL COMPOSITIONS CONTAINING THEM, THEIR PREPARATION METHOD AND THEIR USES

FIELD OF INVENTION

A subject of the present invention is novel derivatives of morphine-6-glucuronide, their preparation method as well as their uses in therapy, in particular as analgesics.

BACKGROUND OF INVENTION

Morphine is currently the most commonly used analgesic in the treatment of medium and high-intensity pain. At the level of the central nervous system three main classes of opioid receptors are distinguished: μ (mu), κ (kappa) and δ (delta). Morphine, like other opioids, mainly has an effect on the central nervous system and the digestive system via μ-opioid receptors. Two sub-types of μ receptors exist: type μ1 with very high affinity and low capacity, and type μ2 with low affinity and high capacity (Pasternak & Wood, 1986. *Life Sci* 38: 1889-1898). The bond with the μ1 receptors causes an analgesic reaction of the supraspinal type and reduction of the turnover of acetylcholine, while the bond with the μ2 receptors leads to an analgesic reaction of the spinal type and is responsible for respiratory depression and the inhibition of intestinal transit.

The mechanisms by which morphine exerts its analgesic action are still not completely clear. It is known that it undergoes a significant metabolism which leads to metabolites, some of which contribute to its analgesic action. The liver appears to be the main site of its biotransformation. Morphine principally undergoes an enantioselective glucuronidation catalyzed by UDP-glucuronyltransferase (UGT) which leads to the formation of two metabolites: morphine-3-glucuronide (hereafter also called "M3G") and morphine-6-glucuronide (hereafter also called "M6G").

It has been demonstrated that the modification of the 3-hydroxy position of morphine reduces analgesic activity, while modification of the 6-hydroxy position can, by contrast, increase analgesic activity (Aderjan & Skopp, 1998, Therapeutic Drug Monitoring 20: 561-569).

Thus, M3G has no affinity for the opioid receptors and does not participate in the analgesic activity of morphine.

On the other hand, morphine-6-glucuronide has a high affinity for the opioid receptors and it has been demonstrated that it has an analgesic effect both in rodents and in humans.

M6G has been described as an analgesic which is more powerful than morphine itself after a central administration (Paul et al., 1989. J Pharmacol. Exp. Ther. 49; 6280-6284; Frances et al., 1992. J Pharmacol. Exp. Ther. 262; 25-31) and has the same activity by systemic route. Studies of the ligand-opiate receptor bond carried out in vitro have shown that M6G bonded with the opioid receptors and that it had 1 to 5 times less affinity for μ receptors than morphine (Christensen & Jorgensen 1987. Pharmacol Toxicol. 60: 75-76; Frances et al., 1992 J Pharmacol. Exp. Ther. 262; 25-31).

Other morphine metabolites, in particular normorphine, have shown some analgesic activity. However, these other metabolites are present in low concentrations and are not capable of contributing in a significant fashion to the overall effect of morphine.

However, although it is very effective, the treatment of pain with morphine has undesirable side effects such as: respiratory depression, inhibition of intestinal transit, nausea, vomiting, and especially dependence syndrome and induction of tolerance.

Therefore it was sought to develop other active substances, presenting an analgesic effectiveness comparable to morphine, but not having all or some of its undesirable side effects.

Of course, due to its analgesic activity described above, it has been proposed to use M6G as a substitute for morphine.

In this regard, reference can be made to International Application WO 95/05831 relating to the use of a pharmaceutical composition for oral administration, containing M6G, for the treatment of pain.

International Application WO 99/64430 describes a method for the synthesis of M6G and its intermediates. U.S. Pat. No. 5,621,087 describes a novel method for the preparation of M6G or some of its derivatives.

M6G, which, as has been seen, has analgesic properties comparable to morphine, has the advantage of reducing nausea and vomiting. However, M6G does not contribute to the prevention of other undesirable effects of morphine, namely respiratory depression and dependence syndrome (Osborne et al., 1992. *Br. J. Clin. Pharmnac* 34: 130-138).

U.S Pat. No. 6,150,524 describes methods for the synthesis of other morphine derivatives, which are said to have strong analgesic properties and which can be administered by oral route.

It is also known that the combination of a compound binding to the μ receptors and a compound binding to the κ receptors, has a powerful analgesic effect without the side effects of physical dependence and respiratory depression (Rothman et al. 2000; J Subst Abuse Treat 19: 277-281; Shook et al., 1990 Am Rev Respir Dis 142: 895-909).

However, to the inventors' knowledge, no analgesic exists with an effectiveness comparable to that of morphine or M6G, but which does not have, or has fewer, side effects, in particular with regard to physical dependence and respiratory depression.

BRIEF SUMMARY OF THE INVENTION

The main subject of the present invention is therefore novel compounds, derived from M6G, which allow this problem to be resolved. More particularly, the compounds of the invention have the advantage of possessing greater affinity for the κ receptors than M6G without however having reduced affinity for the μ receptors in order to obtain a compound having powerful analgesic activity but fewer side effects.

In the context of their research, the inventors have thus been able to determine that the modification of M6G by substitution using a group carrying a thiol function or a sulphur atom allows a significant increase in the affinity for the κ receptors without however reducing the affinity for the μ receptors.

DETAILED DESCRIPTION OF THE INVENTION

The invention thus relates to a compound of formula (A):

(A)

in which:
all of the above entity, with the exception of the substituent X, is called M6G-N($R_2$)$R_1$—S—
$R_1$ represents a linear or branched $C_1$-$C_{10}$ alkyl group, unsubstituted or substituted by at least one substituent, the alkyl chain being optionally interrupted by one or more heteroatoms chosen from O, S and N;
$R_2$ represents hydrogen, a linear or branched $C_1$-$C_5$ alkyl group or an aryl, heteroaryl or ($C_1$-$C_5$) alkylaryl group, unsubstituted or substituted by a $C_1$-$C_4$ alkyl;
X represents hydrogen, an M6G-N($R_2$)$R_1$—S— residue or a polymer linked with the rest of the entity by a spacer arm;
the asymmetric carbons present in the formula (A) can have the R or S configuration.

When $R_1$ represents an alkyl group substituted by one or more substituents, the substituent(s) is (are) chosen for example from: a $C_1$-$C_5$ alkyl group; an amino group; a $COOR_3$ group; a $CONR_3R_4$ group, $R_3$ and $R_4$ in the $COOR_3$ or $CONR_3R_4$ groups independently representing hydrogen, an optionally substituted $C_1$-$C_{20}$ alkyl, an aryl, a heteroaryl or an alkylaryl group; a $C_1$-$C_{20}$ ketone, preferably a $C_1$-$C_{10}$ ketone; a $C_1$-$C_{20}$ aldehyde, preferably a $C_1$-$C_{10}$ aldehyde.

When $R_2$ represents a monocyclic aryl or heteroaryl group, this can for example be chosen from the phenyl, thiophenyl, pyridyl, pyrrolyl, pyrazolyl, furanyl, or indolyl groups. When $R_2$ represents an alkylaryl group, this can for example be benzyl.

Preferred compounds for the purposes of the invention are the compounds of formula (A) in which $R_1$ represents a linear or branched $C_1$-$C_{10}$ alkyl group, in particular methyl, ethyl, propyl or butyl, unsubstituted or substituted by at least one substituent, the alkyl chain being optionally interrupted by one or more heteroatoms chosen from O, S and N, $R_2$ represents hydrogen and X represents hydrogen.

Among these, the compound of formula (A) in which $R_1$ represents —$(CH_2)_2$—, $R_2$ is hydrogen and X is hydrogen is preferred. Such a compound represented in the structure (I) below is called M6G-cysteamide.

(I)

Preferred compounds are those in which X represents an M6G-N($R_2$)$R_1$—S— residue. In this case, the structure (A) corresponds to the oxidized form of the initial structure (A), and in this case is in the dimer form.

The two M6G-N($R_2$)$R_1$—S— residues which constitute the compounds of formula (A) in dimer form can be identical or different.

Particularly advantageous compounds of this type are those in which the two M6G-N($R_2$)$R_1$—S— residues are identical, and the dimeric compounds have a symmetrical structure.

It has been shown in the literature that disulphide bonds, relatively stable in plasma, can be cleaved inside the cells in order to restore a thiol function, and thus could allow an improvement in the properties of the active molecules in vivo (G. Saito et al., Advanced Drug Delivery Reviews, 2003, 55, 199-215).

Preferred compounds according to the invention are compounds of formula (A) in which $R_1$ is as defined above, $R_2$ is hydrogen and X is an M6G-N($R_2$)$R_1$—S— residue as defined above.

A preferred compound of formula (A) in which $R_1$ represents —$(CH_2)_2$—, $R_2$ is hydrogen and X is an M6G-N($R_2$)$R_1$—S— residue in which $R_1$=$(CH_2)_2$ and $R_2$ is hydrogen, represented in the structure (II) below is called M6G-Cya-Cya-M6G. Compound (II) is the oxidized, therefore dimerized, form of compound (I).

(II)

Other advantageous compounds of formula (A) are, for example, those in which:

$R_1$ represents a —CH(COOR$_3$)—CH$_2$— group in which $R_3$ represents hydrogen or an alkyl, in particular methyl, ethyl, propyl or butyl, $R_2$ represents hydrogen and X represents hydrogen or an M6G-N(R$_2$)R$_1$—S— residue in which $R_1$=—CH(COOR$_3$)—CH$_2$— in which $R_3$ is as defined above and $R_2$ is hydrogen;

$R_1$ represents a —CH(CONR$_3$R$_4$)—CH$_2$— group in which $R_3$ and $R_4$ represents hydrogen or an alkyl, in particular methyl, ethyl, propyl or butyl, $R_2$ represents hydrogen and X represents hydrogen or an M6G-N(R$_2$) R$_1$—S— residue in which $R_1$=—CH(CONR$_3$R$_4$)—CH$_2$— in which $R_3$ and $R_4$ are as defined above and $R_2$ is hydrogen;

$R_1$ represents a —CH(COOR$_3$)—C(CH$_3$)$_2$— group in which $R_3$ represents hydrogen or an alkyl, in particular methyl, ethyl, propyl or butyl, $R_2$ represents hydrogen and X represents hydrogen or an M6G-N(R$_2$)R$_1$—S— residue in which $R_1$=—CH(COOR$_3$)—C(CH$_3$)$_2$— in which $R_3$ is as defined above and $R_2$ is hydrogen;

$R_1$ represents a —CH(COOR$_3$)—(CH$_2$)$_2$—C(O)NHCH (R$_5$)—CH$_2$— group, in which $R_3$ represents hydrogen or an alkyl, in particular methyl, ethyl, propyl or butyl, $R_5$ represents —C(O)—NH—CH$_2$—COOR$_3$ in which $R_3$ is as defined above, $R_2$ represents hydrogen and X represents hydrogen or an M6G-N(R2)R1-S— residue in which $R_1$=—CH(COOR$_3$)—(CH$_2$)$_2$—C(O)NHCH (R$_5$)—CH$_2$— in which $R_3$ and $R_5$ are as defined above and $R_2$ represents hydrogen.

Other compounds of interest are those in which X represents a polymer linked with the rest of the entity by a spacer arm.

In fact, it has been shown in the literature that the conjugation of an organic molecule of biological interest with a poly(ethylene glycol) would allow an increase in the plasma half-life of this molecule (R. B. Greenwald et al., Advanced Drug Delivery Reviews, 2003, 55, 217-250).

Preferably, a spacer arm with the formula S—(CH$_2$)$_n$—NH—C(O)— in which n=0 to 4, preferably 2, will be used.

Other types of spacer arms can also be used, such as for example a bivalent organic radical, chosen from the linear or branched $C_1$-$C_{20}$ alkylene groups optionally containing one or more double bonds or triple bonds and/or optionally containing one or more heteroatoms such as O, N, S, P, or one or more carbamoyl or carboxamido group(s); the $C_5$-$C_8$ cycloalkylene groups and the $C_6$-$C_{14}$ arylene groups, said alkylene, cycloalkylene or arylene groups being optionally substituted by alkyl, aryl or sulphonate groups.

Among the compounds in which X represents a polymer linked to the rest of the entity by a spacer arm, the compounds of formula (A) in which $R_1$ represents a —(CH$_2$)$_2$— group, $R_2$ represents hydrogen and X represents a polymer linked with the rest of the entity via a spacer arm of formula —S—(CH$_2$)$_n$—NH—C(O)— in which n=0 to 4, preferably 2, and said polymer is a poly(ethylene glycol) (also called PEG) with a molecular weight (Mw) greater than or equal to 10000, are preferred compounds according to the invention.

The invention also relates, according to a further aspect, to a method for the preparation of the compounds of formula (A).

Said method comprises the stages consisting of reacting morphine-6-glucuronide with a compound of formula (III) NHR$_2$—R$_1$—S—S—R$_1$—NHR$_2$, in which $R_1$ and $R_2$ are as defined above, in the presence of a coupling agent and reducing in situ the disulphide bridge using a reducing agent if necessary (i.e. when X=H in formula (A)).

Preferably, the reaction of morphine-6-glucuronide with the compound of formula (III) takes place in basic medium.

For the preparation of the compounds of formulae (I) or (II), a compound of formula (III) in which $R_2$ is hydrogen and $R_1$ represents a —(CH$_2$)$_2$— group, known as cystamine will be used for example.

As coupling agent, the coupling agents usually used in peptide synthesis, such as benzotriazol-1-yl-oxy-tris-pyrrolidino-phosphonium hexafluorophosphate (PyBOP), dicyclohexylcarbodiimide (DCC), DCC combined with hydroxybenzotriazole (DCC/HOBT) or diisopropylcarbodiimide combined with HOBT (DIPCDI/HOBT) can be mentioned.

Preferably the coupling agent will be used in a molar excess of approximately 1.1 to 4 molar equivalents for 1 molar equivalent of compound of formula (III).

The coupling is preferably carried out at ambient temperature, in a polar solvent such as for example dimethylformamide (DMF), N-methylpyrrolidone (NMP), dichloromethane or acetonitrile.

As reducing agent, tris(2-carboxyethyl)phosphine, triphenylphosphine, tris(hydroxymethyl)-phosphine or dithiothreitol may for example be mentioned.

Preferably the reducing agent will be used in a molar excess of approximately 1.1 to 5 equivalents.

The reduction preferably takes place at ambient temperature and at a pH less than 7.

According to another aspect of the invention, the compound of formula (A) in which X=H can be obtained by a method comprising the stages consisting of reacting morphine-6-glucuronide with a compound of formula (IV) $NHR_2$—$R_1$—SH, in which $R_1$ and $R_2$ are as defined above, in the presence of a coupling agent and reducing in situ the oxidation by-products using a reducing agent.

Preferably, the reaction of morphine-6-glucuronide with the compound of formula (IV) takes place in basic medium.

In particular a compound of formula (IV) can be used in which $R_2$ is hydrogen and $R_1$ represents a —$(CH_2)_2$— group, known as cysteamine. As examples of compounds of formula (IV), cysteine methyl ester, penicillamine or glutathione can also be mentioned.

As coupling agent, the coupling agents usually used in peptide synthesis such as those mentioned above, can be used.

Preferably the coupling agent will be used in a molar excess of approximately 1.1 to 2 molar equivalents for 1 molar equivalent of morphine-6-glucuronide.

The coupling is preferably carried out at ambient temperature, in a polar solvent such as for example dimethylformamide (DMF), N-methylpyrrolidone (NMP), dichloromethane or acetonitrile.

The reducing agent can be chosen from the reducing agents usually used in peptide chemistry such as those mentioned above.

Preferably the reducing agent will be used in a quantity of approximately 0.5 to 5 molar equivalents.

The reduction preferably takes place at ambient temperature and at a pH less than 7.

The invention also relates to a pharmaceutical composition containing as active ingredient a compound of formula (A) as described above or one of its pharmaceutically acceptable salts, and at least one pharmaceutically acceptable vehicle.

By "pharmaceutically acceptable salt", is meant, by way of non-limitative example, an acetate, a sulphate or a hydrochloride.

Advantageously, the pharmaceutical composition according to the invention will be in an appropriate form for an administration:
  by parenteral route, such as for example, in the form of preparations which can be injected by sub-cutaneous, intravenous or intramuscular route;
  by oral route, such as for example, in the form of tablets, coated or not coated, gelatin capsules, powders, granules, suspensions or oral solutions. Such a form for administration by oral route can have either immediate release, or sustained or controlled release. Such forms with sustained or controlled release are described, for example, in the applications EP 253 104 or EP 576 643;
  by rectal route, such as for example, in the form of suppositories;
  by topical route, in particular transdermal route, such as for example, in the form of a patch, a pomade or a gel.
  by intranasal route, such as for example in the form of aerosols and sprays,
  by perlingual route,
  by intraocular route.

The pharmaceutically acceptable vehicle can be chosen from the vehicles conventionally used for each of the administration methods.

The invention also relates to the use of a compound of formula (A) or one of its pharmaceutically acceptable salts for the production of a medicament useful for the treatment of pain, in particular for the treatment of acute pain or chronic pain, neuropathic pain, muscle pain, bone pain, post-operative pain, migraine, cancer pain, lumbar pain, arthrosis pain, pain associated with diabetes or pain associated with AIDS.

The invention is illustrated in a non-limitative way by the examples below.

EXAMPLES

A. Syntheses

Figure 2:
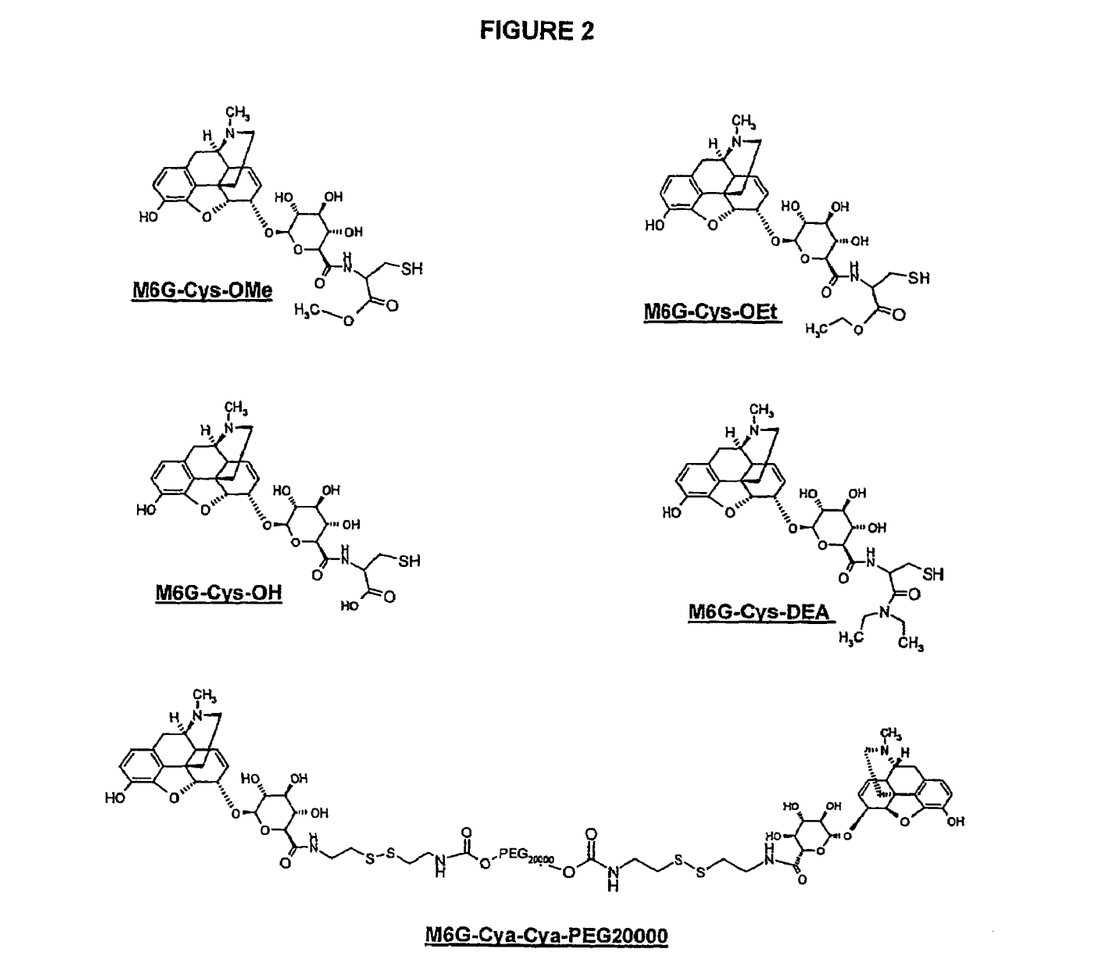
FIG. 2 shows structures of compounds synthesized according to the invention.
Figure 3:
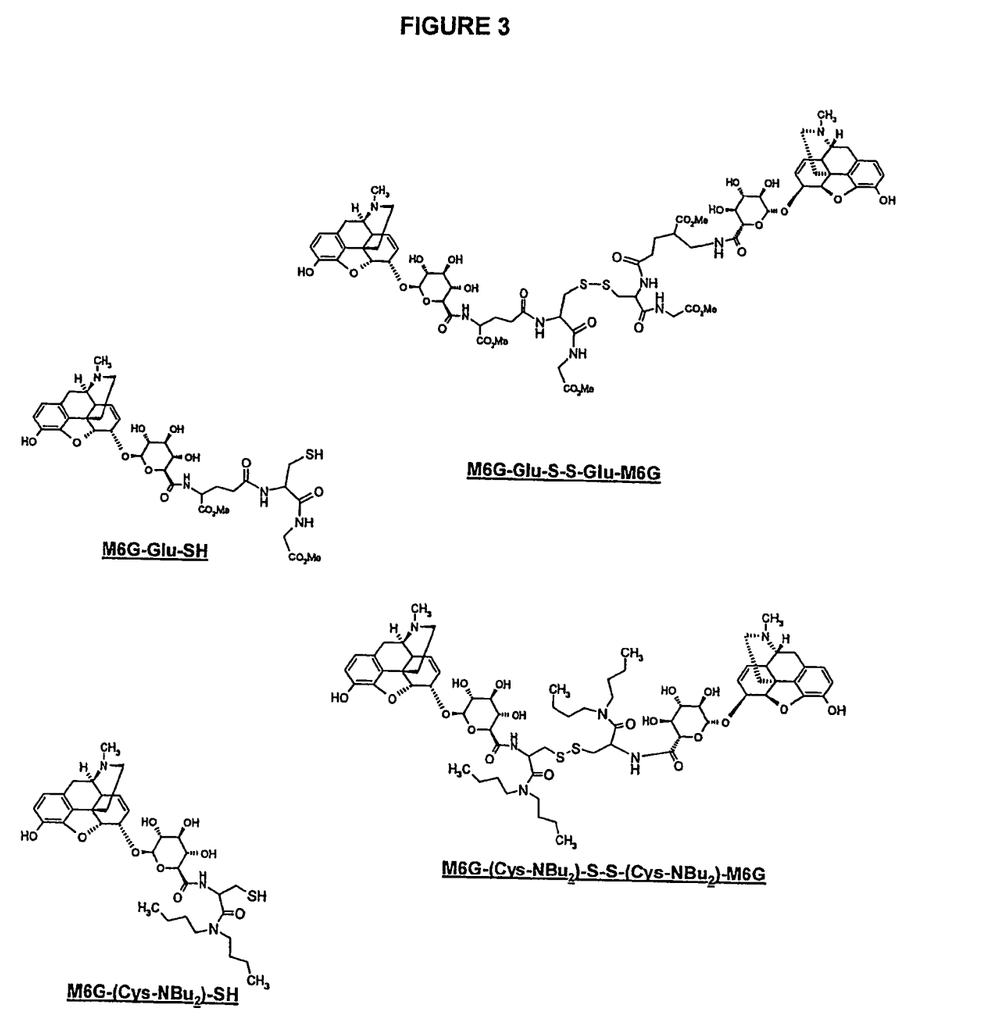
FIG. 3 shows further structures of compounds synthesized according to the invention.

The reactions have been monitored by analytical reversed-phase high-performance liquid chromatography (HPLC) and mass spectrometry (MS). The purities and the identity of the compounds obtained are confirmed by analytical reversed-phase HPLC and by mass spectrometry. The different synthesis routes are carried out according to the diagram represented in FIG. 1. The structures of the compounds synthesized are represented in FIGS. 1 to 3.

Example 1

Synthesis of M6G-cysteamide

Figure 1:
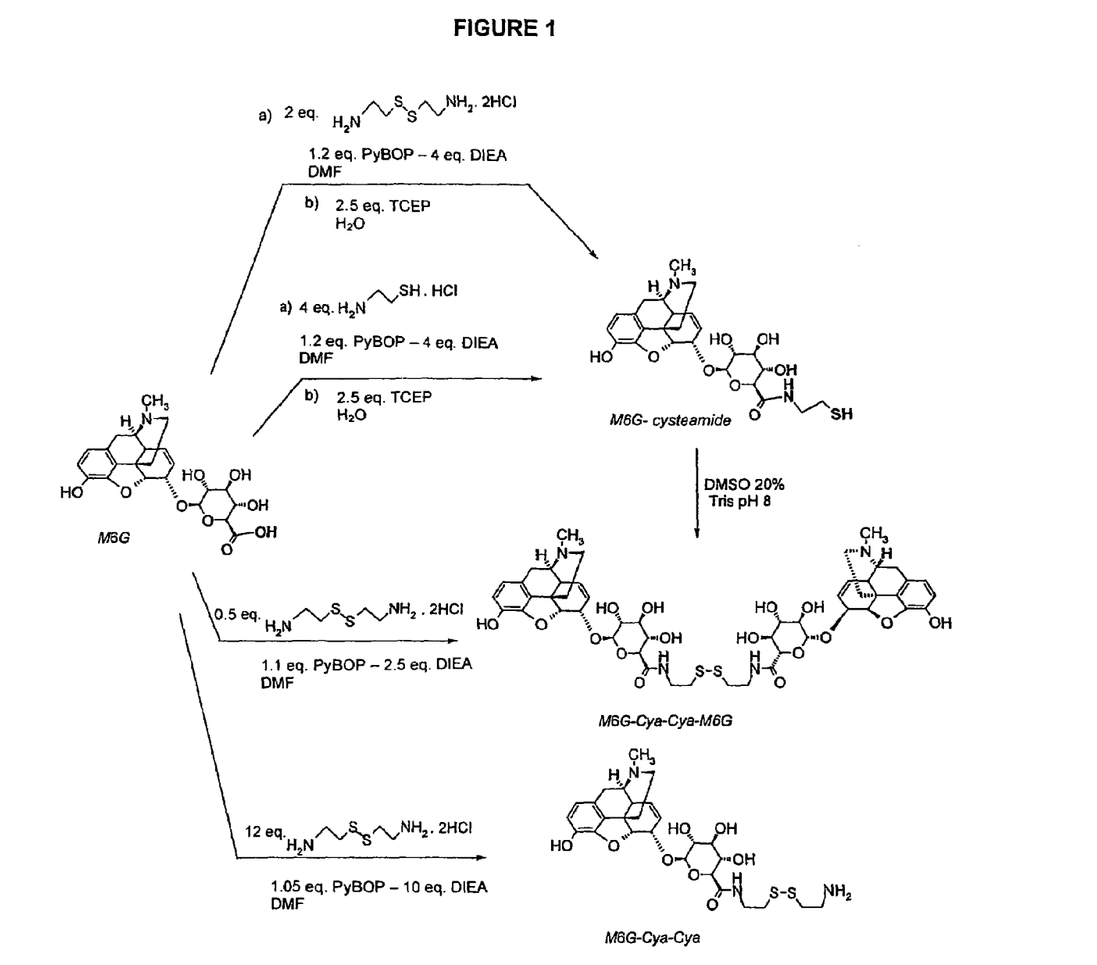
FIG. 1 is a diagram of different synthesis routes of the inventive compounds.

The different synthesis routes are carried out according to the diagram represented in FIG. 1.

Synthesis by Coupling with Cysteamine 4 molar equivalents of cysteamine in its hydrochloride form in dimethylformamide (DMF) at 200 g/l and 4 molar equivalents of diisopropylethylamine (DIEA) were introduced into a reactor (falcon tube). 1 molar equivalent of M6G in powder form and 1.2 molar equivalents of benzotriazol-1-yl-oxy-tris-pyrrolidino-phosphonium hexafluorophosphate (PYBOP) previously solubilized in DMF at 680 g/l were added, it was then verified that the pH was still basic. The reaction takes place for 3 hours under stirring at ambient temperature.

The disulphide bridge of the oxidation by-products generated during coupling in basic medium was then reduced with tris(2-carboxyethyl)phosphine in its hydrochloride form (TCEP) (0.72 molar equivalent) at 150 g/l in a mixture (acetonitrile/$H_2O$ (50/50), trifluoroacetic acid 0.1%). After reacting for 12 hours under stirring, the crude product is then purified by preparative HPLC.

After lyophilization the M6G-cysteamide product is obtained: $[M+H]^+$=521.4—$M_{TFA\ salt}$=634—Yield=66%—Purity 95%.

Synthesis by Coupling with Cystamine 2 molar equivalents of cystamine in its hydrochloride form in DMF at 30 g/l were introduced into a reactor (falcon tube), then 1 molar equivalent of M6G dihydrate and 4 molar equivalents of DIEA were added. It was verified that the pH was basic ($\geq$9). 1.2 molar equivalents of PyBOP previously solubilized in DMF at 230 g/l were added dropwise whilst cooling with an ice bath. The reaction takes place for 3 hours under stirring. The disulphide bridge was then reduced with tris(2-carboxyethyl)phosphine (2.5 molar equivalents) at 215 g/l in ($H_2O$ -trifluoroacetic acid 0.1%). After reacting for 30 minutes under stirring, the crude product is then purified by preparative HPLC.

After lyophilization the M6G-cysteamide product is obtained: $[M+H]^+$=521.2—$M_{TFA\ salt}$=634—Yield=93%—Purity 98%.

Example 2

Synthesis of M6G-Cya-Cya-M6G

The different synthesis routes are carried out according to the diagram represented in FIG. 1.

Synthesis by Coupling with Cystamine 1 molar equivalent of cystamine in its hydrochloride form in DMF at 15 g/l is solubilized in a reactor (falcon tube), then 5 molar equivalents of DIEA and 2 molar equivalents of M6G dihydrate were added. 2.4 molar equivalents of PyBOP previously solubilized in DMF at 230 g/l were added dropwise whilst cooling with an ice bath. The reaction takes place for 12 hours under stirring. The crude product is purified by HPLC.

After lyophilization the M6G-Cya-Cya-M6G product is obtained: $[M+H]^+=1035.7$—$M_{TFA\ salt}=1266$—Yield=80%—Purity 98%.

Synthesis by Oxidation of M6G-cysteamide

M6G-cysteamide was solubilized in a solution of (dimethylsulphoxide 20%–aqueous buffer tris 200 mM pH=8) at 90 g/l in a reactor (falcon tube), then this was reacted for 48 hours under stirring. The crude product is purified by HPLC.

After lyophilization, the M6G-Cya-Cya-M6G product is obtained: $[M+H]^+=1040.1$—$M_{TFA\ salt}=1266$—Yield=95%—Purity 99%.

Example 3

Synthesis of M6G-Cya-Cya-PEG20000

Coupling with Cystamine

The synthesis of M6G-Cya-Cya is carried out according to diagram 1.

12 molar equivalents of cystamine in its hydrochloride form in DMF at 65 g/l were introduced into a reactor (falcon tube), then 10 molar equivalents of DIEA and 1 molar equivalent of M6G dihydrate were added. 1.05 molar equivalents of PyBOP were added and the reaction medium was stirred vigorously for 5 minutes. The reaction takes place for 1 hour under stirring. The crude product is purified by HPLC.

After lyophilization, the M6G-Cya-Cya product is obtained: $[M+H]^+=596.3$—$M_{TFA\ salt}=823$—Yield=69%—Purity 98%.

Coupling with PEG20000

1 molar equivalent of polyethylene glycol 20000 in toluene at 20 g/l were introduced into a flask, then 23 molar equivalents of 4-nitrophenyl chloroformate and DIEA were added. The reaction medium was heated for 12 hours at 55° C. The crude product is purified by crystallization from dichloromethane/diethyl ether. 4-nitrophenyl-PEG-carbonate was obtained with a yield of the order of 95%. 1 molar equivalent of 4-nitrophenyl-PEG-carbonate in dichloromethane at 250 g/l was introduced in a flask, then 2 molar equivalents of M6G-Cya-Cya in DMF at 40 g/l and 5 molar equivalents of DIEA were added. The reaction medium was stirred for 12 hours, the crude product was precipitated from diethyl ether then purification was carried out by crystallization from dichloromethane/diethyl ether.

M6G-Cya-Cya-PEG20000 was obtained with a yield of the order of 85%.

Example 4

Synthesis of M6G-Cys-OEt 4 molar equivalents of cysteine ethyl ester in its hydrochloride form in DMF at 100 g/l and 4 molar equivalents of DIEA were introduced into a reactor (falcon tube). 1 molar equivalent of M6G in powder form and 1.05 molar equivalents of PyBOP previously solubilized in DMF at 109 g/l were added. The reaction takes place for 2 hours under stirring.

The disulphide bridge of the oxidation by-products generated during coupling in basic medium was then reduced with 2 molar equivalents of TCEP at 30 g/l in a mixture (acetonitrile/$H_2O$ -trifluoroacetic acid 0.1% 1/1). After reacting overnight under stirring, the crude product is then purified by preparative HPLC.

After lyophilization the M6G-Cys-OEt product is obtained: $[M+H]^+=593.5$—$M_{TFA\ salt}=706$—Yield=87%—Purity 98%.

Example 5

Synthesis of M6G-Cys-DEA 1 molar equivalent of cysteine diethyl amide in its trifluoroacetate form in DMF at 77 g/l and 4 molar equivalents of DIEA were introduced into a reactor (falcon tube). 1 molar equivalent of M6G dihydrate in powder form, then 1.05 molar equivalents of PyBOP were added. The reaction takes place for 1 hour under stirring.

The disulphide bridge of the oxidation by-products was then reduced with 2 molar equivalents of TCEP at 30 g/l in a mixture ($H_2O$ -trifluoroacetic acid 0.1%). After reacting for 1 hour under stirring, the crude product is purified by preparative HPLC.

After lyophilization the M6G-Cys-DEA product is obtained: $[M+H]^+=620.2$—$M_{TFA\ salt}=733$—Yield=93%—Purity 98%.

Example 6

Synthesis of M6G-Glu-S—S-Glu-M6G

Esterification of the Acid Functions of Glutathione 1 molar equivalent of oxidized glutathione in methanol at 100 g/l and 0.1 molar equivalents of sulphuric acid are introduced into a reactor (Wheaton reactor). The reaction medium is heated at 80° C. under stirring for 4 hours, then the stirring is continued for 15 hours at ambient temperature and the medium is again heated at 80° C. for 6 hours. The crude product is then purified by preparative HPLC.

After lyophilization esterified oxidized glutathione is obtained: $[M+H]^+=669$-$M_{TFA\ salt}=896$—Yield=17%—Purity 76%.

Coupling of M6G 2 molar equivalents of M6G dihydrate in powder form are suspended in DMF at 93 g/l in a reactor (Wheaton reactor). 1 molar equivalent of esterified oxidized glutathione, 2 molar equivalents of PyBOP and 4 molar equivalents of DIEA are added. The reaction takes place for 5 hours under stirring at ambient temperature. The reaction medium is then purified by preparative HPLC.

After lyophilization the M6G-Glu-S-S-Glu-M6G dimer is obtained: $[M+H]^+=1555$—$M_{TFA\ salt}=1782$—Purity 91%.

Example 7

Synthesis of M6G-Glu-SH

Reduction of the M6G-Glu-S-S-Glu-M6G Dimer 1 molar equivalent of M6G-Glu-S-S-Glu-M6G dimer and 3 molar equivalents of TCEP at 88 g/l of an acetonitrile/$H_2O$ (50/50) mixture and trifluoroacetic acid 0.1% are introduced into a reactor (falcon tube). The reaction takes place for 5 hours under stirring at ambient temperature. The crude reaction product is then purified by preparative HPLC.

After lyophilization, the M6G-Glu-SH product is obtained: $[M+H]^+=779$—$M_{TFA\ salt}=892$—Yield=100%—Purity 95%.

Example 8

Synthesis of M6G-(Cys-NBu$_2$)-S—S-(Cys-NBu$_2$)-M6G

Coupling of (Boc-Cys-OH)$_2$ with Di-n-butylamine 1 molar equivalent of (Boc-Cys-OH)$_2$ in DMF at 105 g/l, 2.2 molar equivalents of Di-n-butylamine, 2.2 molar equivalents of 2-(1-H-9-azabenzotriazol-1-yl)-1,1,3,3-tetramethyluronium hexafluorophosphate (HATU) and 2.2 molar equivalents of DIEA are introduced into a reactor (falcon tube). The reaction takes place for 60 minutes under stirring at ambient temperature.

The tert-butoxycarbonyl protective group is cleaved with a mixture of trifluoroacetic acid/triisopropylsilane (94/6) at 26 g/l. The reaction medium is stirred for 3 hours at ambient temperature. The medium is then diluted in an acetonitrile/$H_2O$ (50/50) mixture and lyophilized then purified by preparative HPLC.

After lyophilization, the (H-Cys-NBU$_2$)$_2$ product is obtained: $[M+H]^+=463$—$M_{TFA\ salt}=690$—Yield=83%—Purity 98%.

Coupling of the M6G 2 molar equivalents of M6G dihydrate in DMF at 99 g/l are introduced into a reactor. 1 molar equivalent of (H-Cys-NBu$_2$)$_2$ product, 4 molar equivalents of DIEA and 2 molar equivalents of PyBOP are added. The reaction medium is stirred at ambient temperature for 1 hour. The crude product is then purified by preparative HPLC.

After lyophilization the M6G-(Cys-NBu$_2$)-S—S-(Cys-NBu$_2$)-M6G dimer is obtained: $[M+H]^+=1349$—$M_{TFA\ salt}=1576$—Yield=36%—Purity 90%.

Example 9

Synthesis of M6G-(Cys-NBU$_2$)—SH

Reduction of the M6G-(Cys-NBu$_2$)-S—S-(Cys-NBu$_2$)-M6G dimer 1 molar equivalent of M6G-(Cys-NBu$_2$)-S—S-(Cys-NBU$_2$)-M6G and 3 molar equivalents of TCEP at 85 g/l of an acetonitrile/$H_2O$ (50/50) mixture and trifluoroacetic acid 0.1% are introduced into a reactor (falcon tube).

After reacting for 4 hours under stirring at ambient temperature, the crude reaction product is purified by preparative HPLC.

After lyophilization, the M6G-(Cys-NBu$_2$)-SH product is obtained: $[M+H]^+=676$—$M_{TFA\ salt}=789$—Yield=85.8%—Purity 93%.

Example 10

Synthesis of M6G-Cys-OMe 2 molar equivalents of cystine dimethyl ester in hydrochloride form in DMF at 68 g/l and 4 molar equivalents of DIEA are introduced into a reactor (falcon tube). The reaction medium is stirred for 2 hours at ambient temperature. 1 molar equivalent of M6G dihydrate in powder form and 1.2 molar equivalents of PyBOP are added. The reaction takes place for 3 hours under stirring at ambient temperature. The disulphide bridge is then reduced with 2 molar equivalents of TCEP at 11.5 g/l in a $H_2O$/trifluoroacetic acid 0.1% mixture. The reaction medium is stirred overnight at ambient temperature. The crude product is purified by preparative HPLC.

After lyophilization the M6G-Cys-OMe product is obtained: $[M+H]^+=579$—$M_{TFA\ salt}=692$—Yield=83%—Purity 98%.

Example 11

Synthesis of M6G-Cys-OH 1 molar equivalent of M6G-Cys-OMe in water at 69 g/l and 3 molar equivalents of lithium hydroxide are introduced into a reactor. The reaction takes place under stirring at ambient temperature overnight.

The disulphide bridge of the oxidation by-product is reduced with 3 molar equivalents of TCEP at 30 g/l in a $H_2O$/trifluoroacetic acid 0.1% mixture.

The reaction medium is stirred for 30 minutes at ambient temperature. The crude product is then purified by preparative HPLC.

After lyophilization the M6G-Cys-OH product is obtained: $[M+H]^+=565$—$M_{TFA\ salt}=678$—Yield=42%—Purity 98%.

B: Study of the Analgesic Effect

For this study, the so-called "tail flick" test was used.

This test consists of placing a mouse's tail in front of an infrared source at a given time after the administration of the product being tested, taken as time 0. The light is focussed on the ventral surface of the tail so as to produce a surface temperature of 55° C. The latency period (reaction time) between the administration of the product being tested and the moment when the mouse moves its tail is then measured.

The compounds studied, namely M6G, morphine and the derivatives according to the invention were administered by intravenous route at doses of 0.25 to 5 mg/kg equivalents (5 to 10 mice per group). Three measurements were made before administration of the product being tested in order to obtain a base period. The latency period for one mouse was measured at different times ranging from 15 minutes to 360 minutes after the injection of the product. A maximum time of 10 seconds was chosen as the maximum reaction time.

The results obtained are represented by the curves of FIGS. 4 to 12, in which the measurement times (min) appear on the abscissa, and on the ordinates, the reaction times(s). The doses of products being tested are expressed in mg equivalents of M6G.

Figure 4:
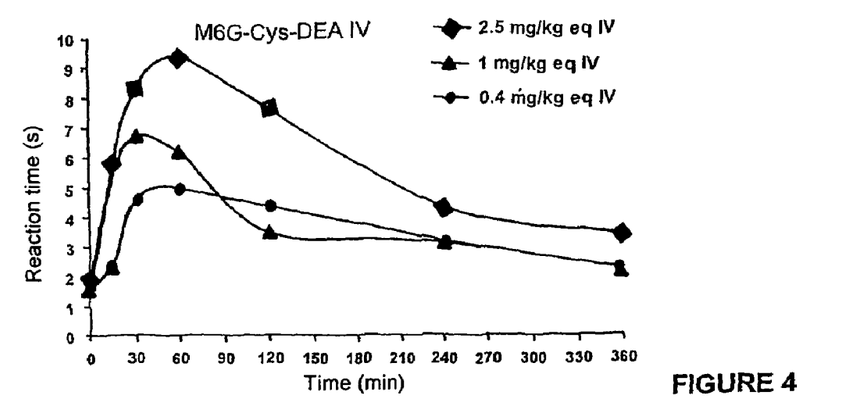
FIG. 4 is a plot of the activity of a M6G-Cys-DEA derivative.

The following symbols are used in the figures for the different dosages:

FIG. 4 (activity of the M6G-Cys-DEA derivative)

-♦-2.5 mg/kg eq; -▲-1 mg/kg eq; -●-0.4 mg/kg eq

Figure 5:
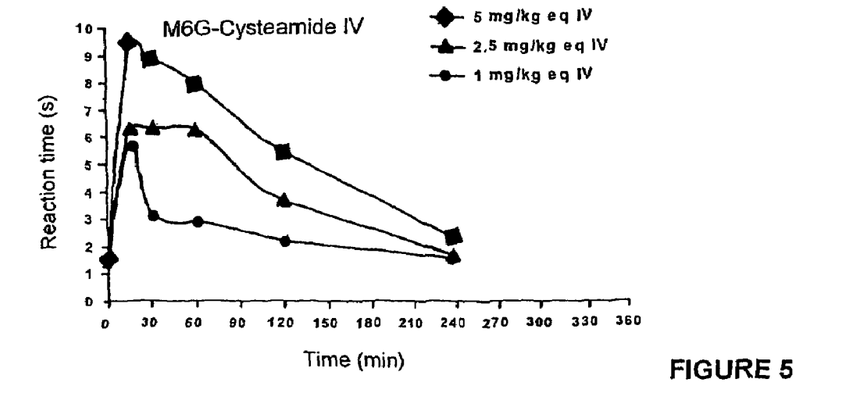
FIG. 5 is a plot of the activity of a M6G-cysteamide derivative.

FIG. 5 (activity of the M6G-cysteamide derivative)

Figure 6:
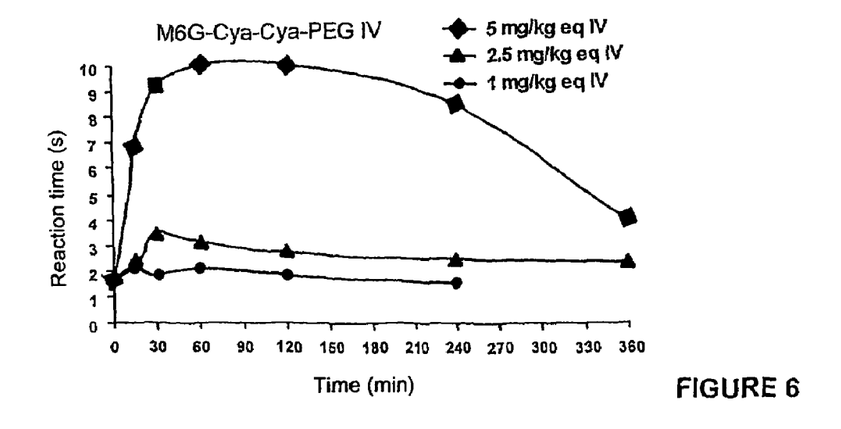
FIG. 6 is a plot of the activity of a M6G-Cya-Cya-PEG derivative.

-♦-5 mg/kg eq; -▲-2.5 mg/kg eq; -●-1 mg/kg eq;

FIG. 6 (activity of the M6G-Cya-Cya-PEG derivative)

Figure 7:
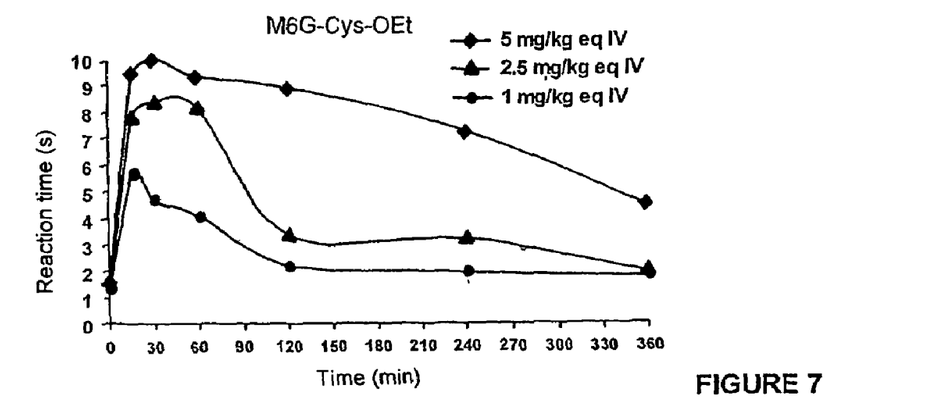
FIG. 7 is a plot of the activity of a M6G-Cys-OEt derivative.

-♦-5 mg/kg eq; -▲-2.5 mg/kg eq; -●-1 mg/kg eq;

FIG. 7 (activity of the M6G-Cys-OEt derivative)

-♦-5 mg/kg eq; -▲-2.5 mg/kg eq; -●-1 mg/kg eq

Figure 8:
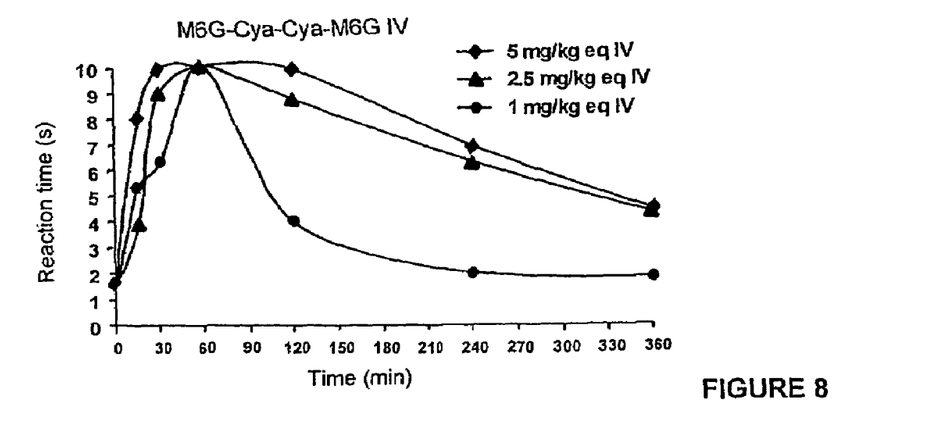
FIG. 8 is a plot of the activity of a M6G-Cya-Cya-M6G derivative.

FIG. 8 (activity of the M6G-Cya-Cya-M6G derivative)

-♦-5 mg/kg eq; -▲-2.5 mg/kg eq; -●-1 mg/kg eq

Figure 9:
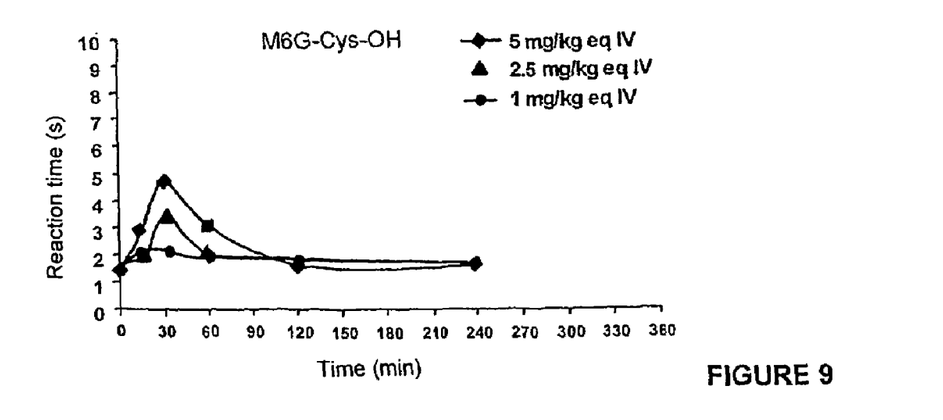
FIG. 9 is a plot of the activity of a M6G-Cys-OH derivative.

FIG. 9 (activity of the M6G-Cys-OH derivative)

-♦-5 mg/kg eq; -▲-2.5 mg/kg eq; -●-1 mg/kg eq

Figure 10:
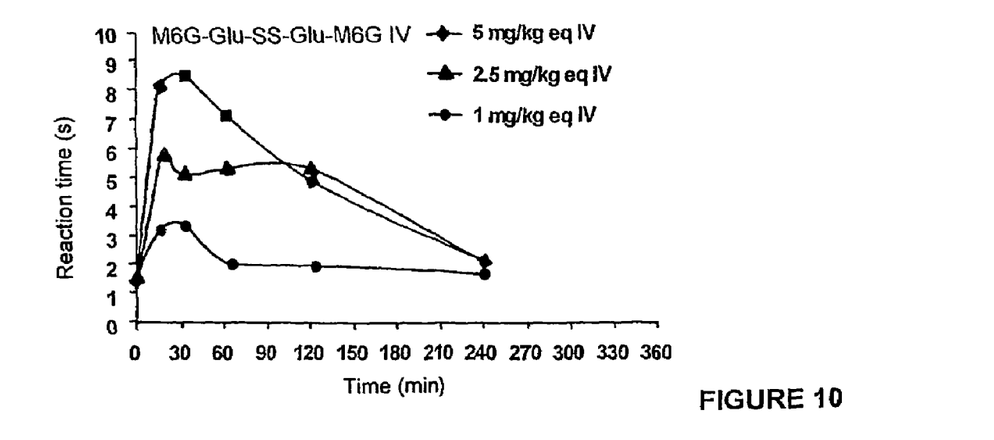
FIG. 10 is a plot of the activity of a M6G-Glu-SS-Glu-M6G derivative.

FIG. 10 (activity of the M6G-Glu-SS-Glu-M6G derivative)

-♦-5 mg/kg eq; -▲-2.5 mg/kg eq; -●-1 mg/kg eq

Figure 11:
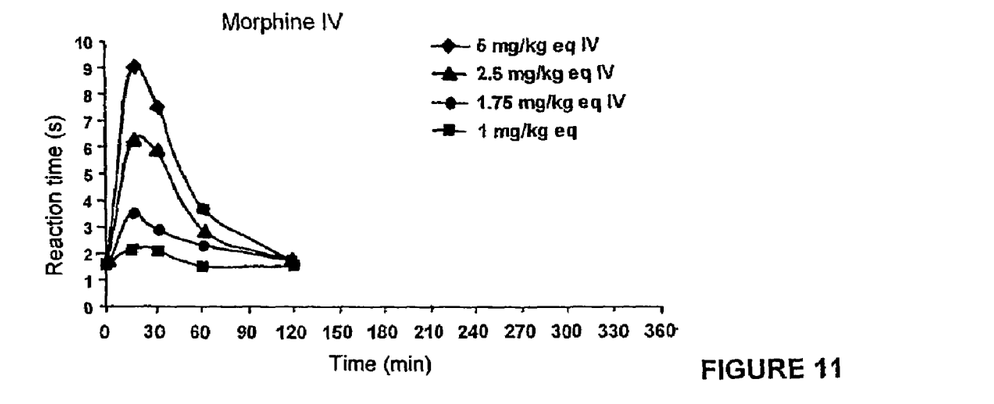
FIG. 11 is a plot of the activity of morphine.

FIG. 11 (morphine activity)

-♦-5 mg/kg eq; -▲-2.5 mg/kg eq; -●-1.75 mg/kg eq

-■-1 mg/kg

Figure 12:
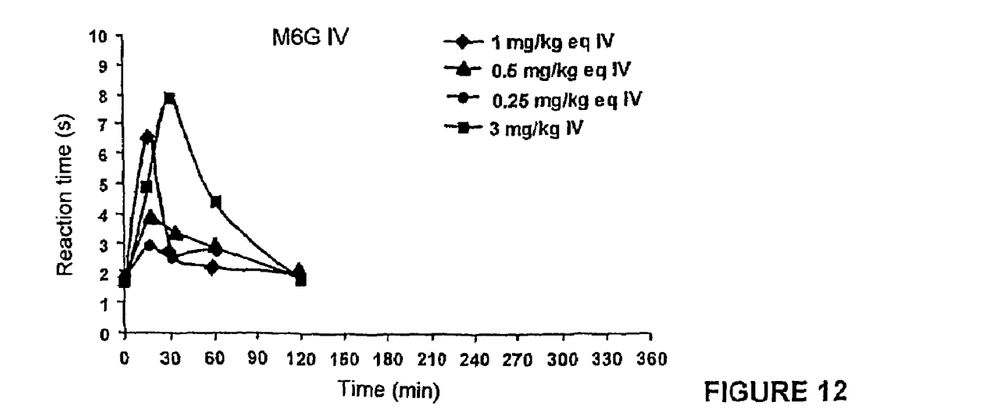
FIG. 12 is a plot of the activity of M6G.

FIG. 12 (M6G activity)

-♦-1 mg/kg eq; -▲-0.5 mg/kg eq; -●-0.25 mg/kg eq

-■-3 mg/kg

The results show that the M6G derivatives according to the invention have an analgesic activity at least similar to M6G and morphine. The $ED_{50}$, the dose which induces 50% of the analgesic effect, is comprised between 0.3 and 2.5 mg eq./kg for the derivatives according to the invention, compared with 0.55 and 2.65 for M6G and morphine respectively.

Moreover, it is observed that for most of the derivatives according to the invention, the analgesic activity lasts much longer. In fact, for M6G and morphine, the duration of the action is approximately 100 minutes while for M6G-Cya-Cya-M6G for example, the duration of the action is 360 minutes.

C: Study of the Affinity to the Opioid Receptors

C. 1/Operating Method

The affinity of M6G and of morphine was compared to that of the M6G derivatives according to the invention for the opioid receptors μ (mu) and κ (kappa).

In order to determine the affinity to the μ receptors, homogenates of rat cerebral cortex membrane (200 μg of protein) were incubated with either M6G, or morphine or the compound according to the invention and 1 nM of [$^3$H][D-Ala$^2$, N-MePhe$^4$, Gly(ol)$^5$]enkephalin (DAMGO) for 60 minutes at 22° C. in a buffer containing 50 mM Tris-HCl [pH 7.7].

In order to determine the affinity to the κ receptors, homogenates of guinea-pig cerebellum membrane (250 μg of protein) were incubated with either M6G, or morphine or the compound according to the invention and 0.7 nM [$^3$H]U 69593 (80 minutes at 22° C.) in a buffer containing 50 mM Tris-HCl [pH 7.4], 10 mM $MgCl_2$, 1 mM EDTA. Concentrations of M6G, morphine and the compound according to the invention of $10^{-14}$ to $10^{-6}$ M were used.

The non-specific binding was determined by means of the addition to the labelled ligands of naloxone 10 μM.

After incubation, the samples were filtered on glass fibres (GF/B, Packard) previously incubated with 0.3% polyethyleneimine and rinsed several times with 50 mM of cold Tris-HCl using a "96-sample cell harvester" (Unifilter, Packard). The filters were then dried and the radioactivity counted.

C. 2/Results

The results are shown in Table 1 below.

TABLE 1

| | Affinity to the μ and K receptors (Ki expressed in nM). | |
|---|---|---|
| Compound | μ receptors | K receptors |
| Morphine | 12.43 | 155.15 |
| M6G | 13.63 | 223.91 |
| M6G-cysteamide | 2.35 | 4.49 |
| M6G-Cys-OMe | 1.04 | 14.02 |
| M6G-Cys-OEt | 1.17 | 11.24 |
| M6G-Cys-DEA | 0.36 | 1.90 |
| M6G-Cya-Cya-M6G | 0.38 | 6.22 |
| M6G-Cya-Cya-PEG200000 | 0.92 | 0.72 |

The results show that:

M6G binds with the μ receptors with a Ki of 13.63 nM indicating an affinity for these receptors. On the other hand, the Ki value for the κ receptors, of the order of 224 nM indicates a low affinity for these receptors.

the affinity of the compounds according to the invention for the κ receptors (Ki=0.72 to 14.02) is increased in a spectacular way compared to that of M6G (up to 310 times), as a result of the chemical modification, without the affinity for the μ receptors being reduced. Indeed, an increase in this affinity for the μ receptors of a factor of approximately 10 is observed.

The invention claimed is:

1. Compound of formula (A):

in which:

all of formula (A), with the exception of the substituent X, is called M6G-N($R_2$)$R_1$—S—

$R_1$ is a linear or branched $C_1$-$C_{10}$ alkyl group, unsubstituted or substituted by at least one substituent, the alkyl chain being optionally interrupted by one or more heteroatoms including O, S or N;

$R_2$ is hydrogen, a linear or branched $C_1$-$C_5$ alkyl group or an aryl, heteroaryl or ($C_1$-$C_5$) alkylaryl group, unsubstituted or substituted by a $C_1$-$C_4$ alkyl;

X is hydrogen, an M6G-N($R_2$)$R_1$—S— residue or a polymer linked with the rest of formula (A) by a spacer arm;

the asymmetric carbons present in the formula (A) can have the R or S configuration, or pharmaceutically acceptable salts of formula (A).

2. Compound according to claim 1, wherein X is an M6G-N($R_2$)$R_1$—S— residue, the two M6G-N($R_2$)$R_1$—S— residues constituting the compounds of formula (A) in dimer form being identical or different.

3. Compound according to claim 1, wherein $R_2$ is hydrogen, and

X is hydrogen.

4. Compound according to claim 1 or 2, characterized in that wherein $R_2$ is hydrogen, and X is an M6G-N($R_2$)$R_1$—S— residue in which $R_1$ and $R_2$ are as defined above.

5. Compound according to claims 1, wherein $R_1$ is an alkyl group substituted by one or more substituents including: a $C_1$-$C_5$ alkyl group; an amino group; a $COOR_3$ group; a $C_1$-$C_{20}$ ketone; a $C_{1-C20}$ aldehyde; or a $CONR_3R_4$ group, wherein $R_3$ and $R_4$ are each independently hydrogen, an optionally substituted $C_1$-$C_{20}$ alkyl, an aryl, a heteroaryl or an alkylaryl group.

6. Compound according to claim 1 or 3, wherein $R_1$ is —$(CH_2)_2$—, $R_2$ is hydrogen and X is hydrogen.

7. Compound according to claim 1 or 2, wherein $R_1$ is —$(CH_2)_2$—, $R_2$ is hydrogen and X is an M6G-N($R_2$)$R_1$—S— residue in which $R_1$=—$(CH_2)_2$— and $R_2$ is hydrogen.

8. Compound according to claim 1 or 2, wherein $R_1$ is a —CH(COOR$_3$)—CH$_2$— group in which $R_3$ is hydrogen, methyl, ethyl, propyl or butyl, $R_2$ is hydrogen, X is hydrogen or an M6G-N($R_2$)$R_1$—S— residue in which $R_1$=—CH(COOR$_3$)—CH$_2$— in which $R_3$ is as defined above and $R_2$ is hydrogen.

9. Compound according to claim 1 or 5, wherein $R_1$ is a —CH(CONR$_3$R$_4$)—CH$_2$— group in which $R_3$ and $R_4$ are hydrogen, methyl, ethyl, propyl or butyl, $R_2$ is hydrogen, X is hydrogen or an M6G-N($R_2$)$R_1$—S— residue in which $R_1$=—CH(CONR$_3$R$_4$)—CH$_2$— in which $R_3$ and $R_4$ are as defined above and $R_2$ is hydrogen.

10. Compound according to claim 1 or 5, wherein $R_1$ is a —CH(COOR$_3$)—C(CH$_3$)$_2$— group in which $R_3$ is hydrogen, methyl, ethyl, propyl or butyl, $R_2$ is hydrogen X is hydrogen or an M6G-N($R_2$)$R_1$—S— residue in which $R_1$=—CH(COOR$_3$)—C(CH$_3$)$_2$— in which $R_3$ is as defined above and $R_2$ is hydrogen.

11. Compound of formula (A):

(A)

in which:

all of formula (A), with the exception of the substituent X, is called M6G-N($R_2$)$R_1$—S— wherein $R_1$ is a —CH(COOR$_3$)—(CH$_2$)$_2$—C(O)NHCH(R$_5$)—CH$_2$— group, in which $R_3$ is hydrogen, methyl, ethyl, propyl or butyl and $R_5$ is —C(O)—NH—CH$_2$—COOR$_3$, $R_2$ is hydrogen X is hydrogen or an M6G-N($R_2$)$R_1$—S— residue in which $R_1$=—CH(COOR$_3$)—(CH$_2$)$_2$—C(O)NHCH(R$_5$)—CH$_2$— in which $R_3$ and $R_5$ are as defined above and $R_2$ is hydrogen.

12. Compound according to claim 1, wherein $R_1$ is a —(CH$_2$)$_2$— group, $R_2$ is hydrogen X is a polymer linked to the rest of the entity by a spacer arm of formula —S—(CH$_2$)$_n$—NH—C(O)— in which n=0 to 4 and said polymer is a polyethylene glycol of molecular weight (Mw) greater than or equal to 10000.

13. Method for the preparation of a compound of formula (A) according to claim 1, comprising reacting morphine-6-glucuronide with a compound of formula (III) NHR$_2$—R$_1$—S—S—R$_1$—NHR$_2$, in which R$_1$ and R$_2$ are as defined above, in the presence of a coupling agent, and reducing the disulphide bridge using a reducing agent if necessary.

14. Method for the preparation of a compound of formula (A) according to claim 1, in which X=H, comprising reacting morphine-6-glucuronide with a compound of formula (IV) NHR$_2$—R$_1$—SH, in which R$_1$ and R$_2$ are as defined above, in the presence of a coupling agent and reducing in situ the oxidation by-products using a reducing agent.

15. Method of claim 13 or 14, wherein the coupling agent includes benzotriazol-1-yl-oxy-tris-pyrrolidino-phosphonium hexafluorophosphate (PyBOP), dicyclohexylcarbodiimide (DCC), DCC combined with hydroxybenzotriazole (DCC/HOBT) or diisopropylcarbodiimide combined with HOBT (DIPCDI/HOBT).

16. Method claim 13 or 14, wherein the reducing agent includes tris(2-carboxyethyl)phosphine, triphenylphosphine, tris(hydroxymethyl)-phosphine or dithiothreitol.

17. Pharmaceutical composition including a compound of formula (A) according to claim 1 and a pharmaceutically acceptable vehicle.

18. Pharmaceutical composition according to claim 17 which is in a form that can be administered by parenteral route.

19. Pharmaceutical composition according to claim 17, which is in a form of a preparation that can be injected by sub-cutaneous, intravenous or intramuscular route.

20. Pharmaceutical composition according to claim 19, which is in a form that can be administered by oral route.

21. Pharmaceutical composition according to claim 20, which has a sustained or controlled activity.

22. A method for treating pain comprising administering a compound according to claim 1 to a human.

23. A method for treating pain comprising administering a pharmaceutical composition according to claim 17 to a human.

* * * * *